United States Patent [19]

Thompson, Jr.

[11] Patent Number: 5,715,943
[45] Date of Patent: Feb. 10, 1998

[54] REUSABLE STERILIZATION POUCH AND ITS METHOD OF PRODUCTION

[75] Inventor: Thomas H. Thompson, Jr., Missoula, Mont.

[73] Assignee: Thompson Dental Mfg Co, Inc., Missoula, Mont.

[21] Appl. No.: 649,996

[22] Filed: May 16, 1996

Related U.S. Application Data

[63] Continuation-in-part of Ser. No. 375,793, Jan. 20, 1995, abandoned, and Ser. No. 511,110, Aug. 4, 1995.

[51] Int. Cl.$^6$ ............................................. B65D 85/28
[52] U.S. Cl. .................... 206/363; 206/439; 206/459.5; 383/91
[58] Field of Search .................... 206/438, 363, 206/459.5, 439; 383/86, 91, 905

[56] References Cited

U.S. PATENT DOCUMENTS

| | | | |
|---|---|---|---|
| 3,299,927 | 1/1967 | Clarizio | 383/91 |
| 3,315,877 | 4/1967 | Grevich | 229/65 |
| 3,446,420 | 5/1969 | Rinecker | 229/62 |
| 3,545,668 | 12/1970 | Hultberg | 229/65 |
| 3,655,118 | 4/1972 | Rinecker | 229/62 |
| 3,728,839 | 4/1973 | Glick | 53/21 FC |
| 3,939,971 | 2/1976 | Tulis | 206/205 |
| 3,942,634 | 3/1976 | Gandi | 206/210 |
| 3,958,750 | 5/1976 | Prybeck | 229/56 |
| 4,041,203 | 8/1977 | Brock | 428/157 |
| 4,091,921 | 5/1978 | Lewis | 206/363 |
| 4,117,934 | 10/1978 | Mowli | 383/905 |
| 4,194,622 | 3/1980 | Lewis | 206/363 |
| 4,408,643 | 10/1983 | Laske | 383/70 |
| 4,437,567 | 3/1984 | Jeng | 206/210 |
| 4,482,053 | 11/1984 | Alpern et al. | 206/439 |
| 4,510,621 | 4/1985 | Sak et al. | 383/89 |
| 4,644,586 | 2/1987 | Padgett | 383/102 |
| 4,706,297 | 11/1987 | Ausnit | 383/63 |
| 5,041,264 | 8/1991 | Williams | 422/28 |
| 5,048,692 | 9/1991 | Handler et al. | 206/618 |
| 5,082,636 | 1/1992 | Anderson | 422/294 |
| 5,344,017 | 9/1994 | Wittrock | 206/459.1 |

FOREIGN PATENT DOCUMENTS

| | | | |
|---|---|---|---|
| 2598886 | 11/1987 | France | A01N 1/02 |
| 1254557 | 11/1971 | United Kingdom . | |
| WO 87/02646 | 5/1987 | WIPO | B65D 33/22 |
| WO 93/15969 | 8/1993 | WIPO | B65D 33/24 |

OTHER PUBLICATIONS

Meer Dental Supply Catalog, 1991, p. 176.
Henry Schein Inc., 1991 Dental Catalog, p. 24.
Veratex Discount Dental, 1984 Catalog, p. 138.
Becker–Parkins Dental Equipment Supply Catalog, 1990, inside front cover.
Hu–Friedy Dental Mfg. Co., 1991 Catalog, p. 3–IMS.

*Primary Examiner*—David T. Fidei
*Attorney, Agent, or Firm*—Harry M. Cross, Jr.

[57] ABSTRACT

A reusable sterilization pouch 10 comprises a pair of sheets 7, 9 that provide first and second sides 12, 14 of the pouch, and a closure 16. The sheets are edge-bonded along both side edges and along the bottom edge to provide sealing seams 13, 15 and 17, respectively. The closure 16 comprises a transverse open-ended channel 19 extended across the top of the pouch and a closure strip 18 that is inserted through the channel 19. Channel 19 is large enough that closure strip 18 can be manually inserted therethrough; channel 19 may be slightly larger, but it should not be so large that closure strip 18 would be so loosely contained that it could fall out of the channel when the pouch 10 is held or tilted on edge. Channel 19 is formed by doubling or folding one end of the sheet 9, comprising side 14, back onto itself and edge-bonding the overlap to provide a transverse seam 20. The pouch is sealed by folding the closure 16 down several times and then crimping the strip 18 around the ends of the folds and against the back side 14 of the pouch.

6 Claims, 6 Drawing Sheets

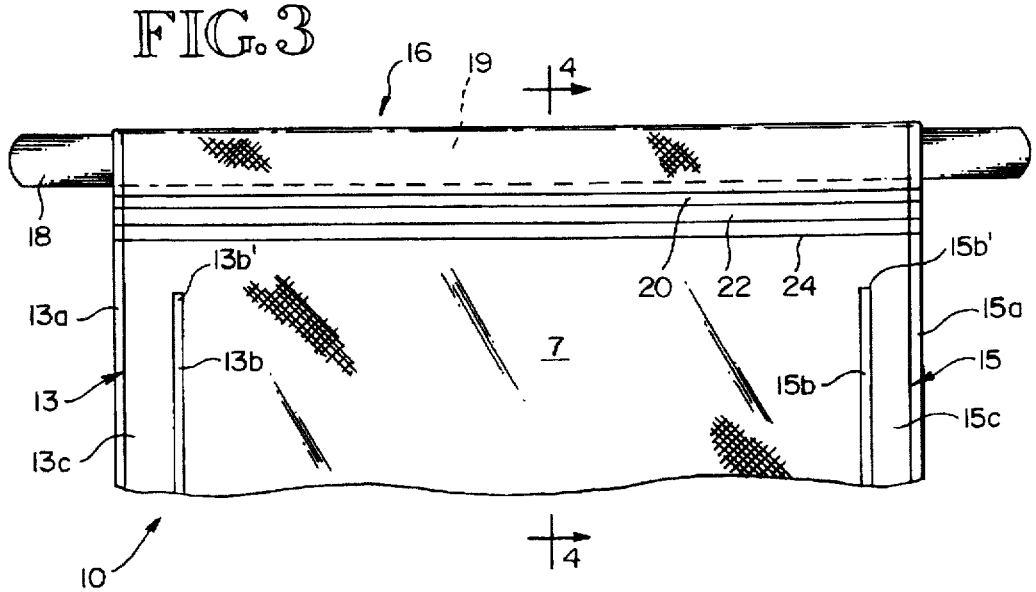
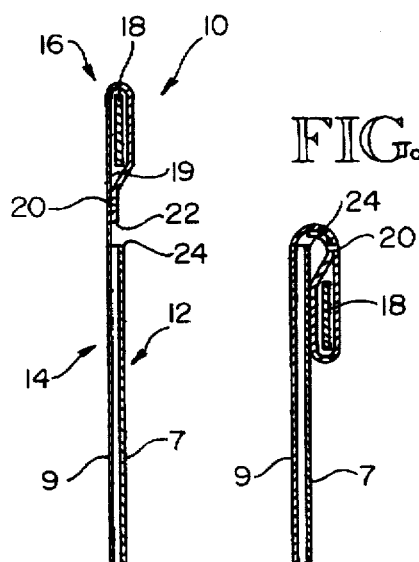
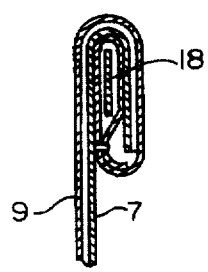
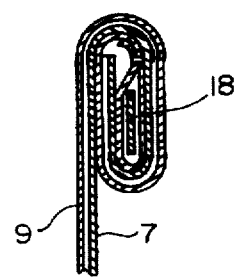
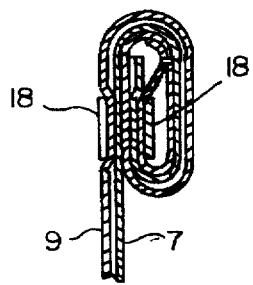

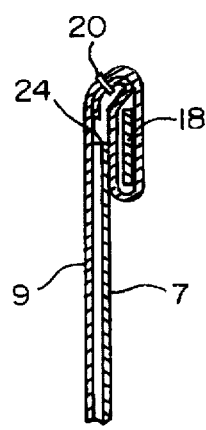
FIG. 5A
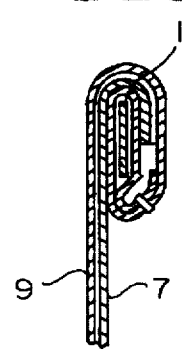
FIG. 6A
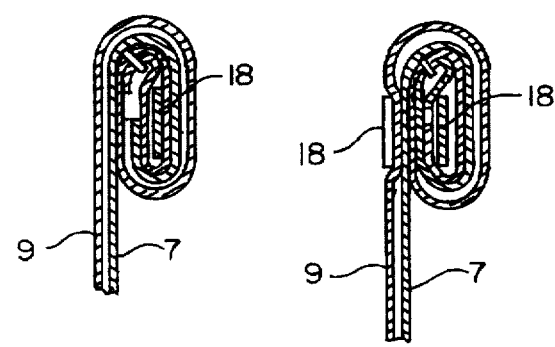
FIG. 7A
FIG. 8A

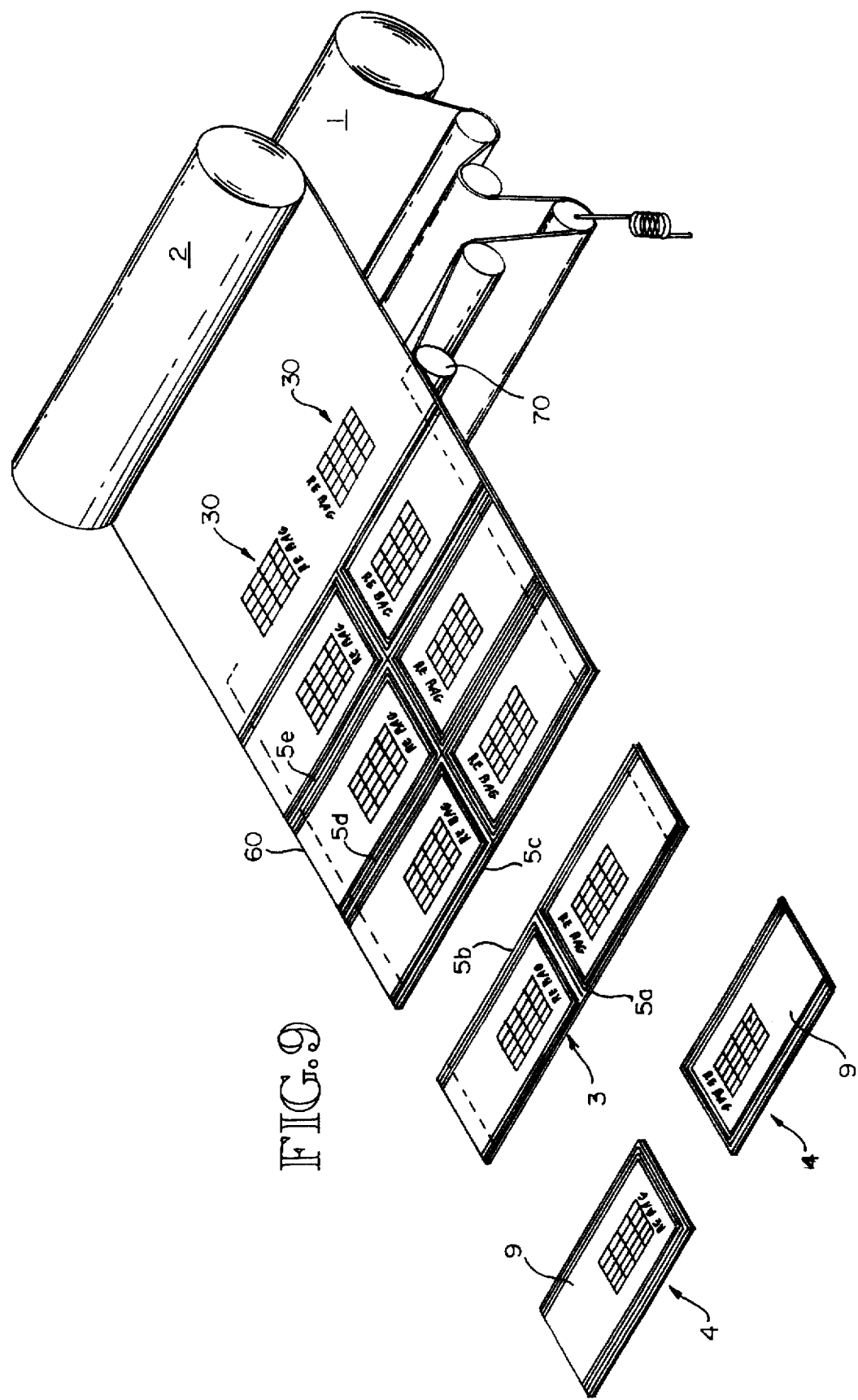

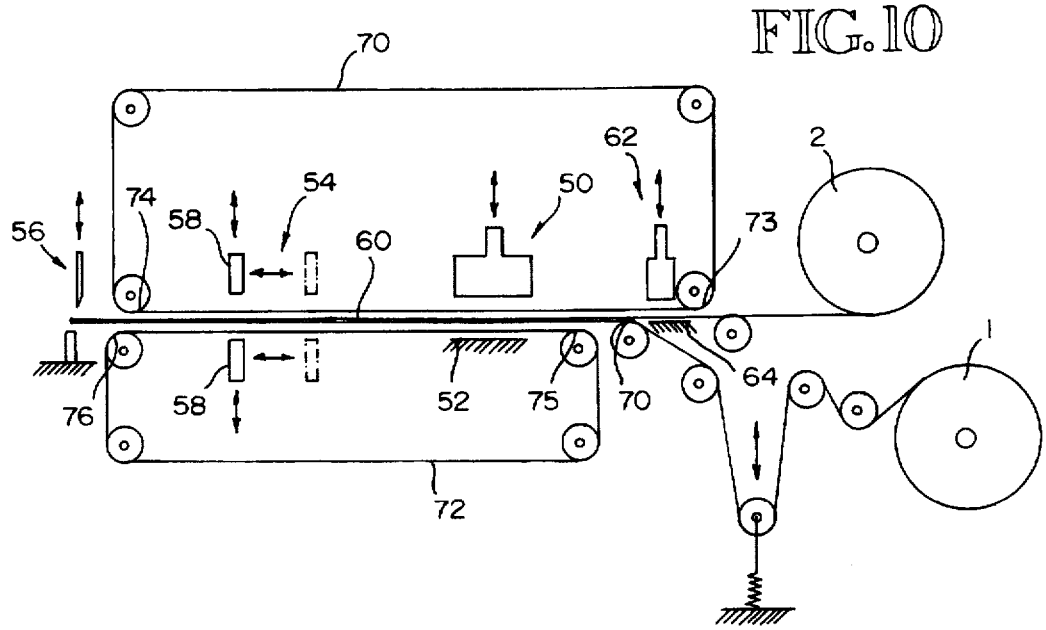
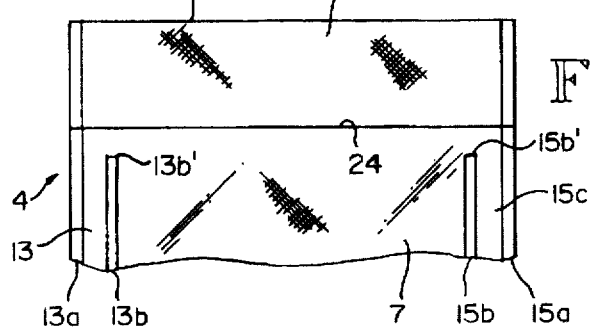
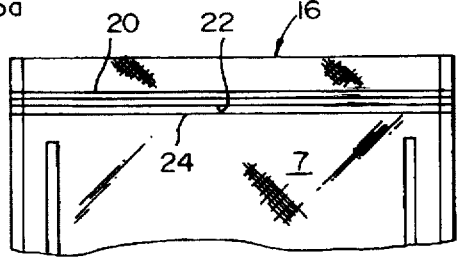
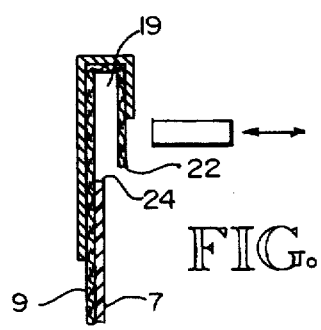
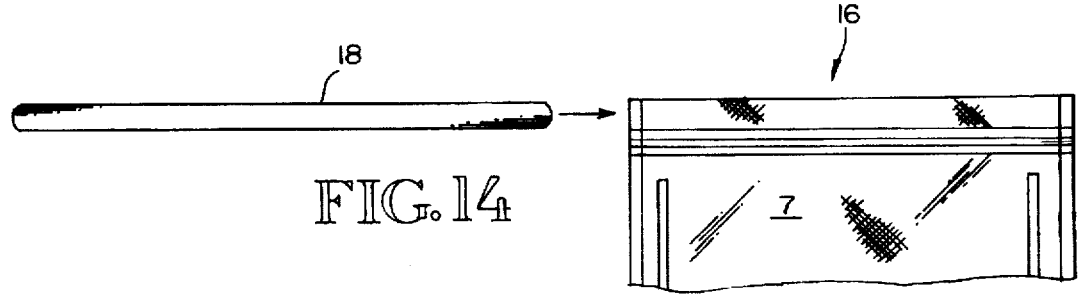

5,715,943

1

REUSABLE STERILIZATION POUCH AND ITS METHOD OF PRODUCTION

CROSS-REFERENCE TO RELATED APPLICATIONS

This application is a continuation-in-part to my applications Ser. No. 08/375,793, filed Jan. 20, 1995, now abandoned, and Ser. No. 08/511,110, filed Aug. 4, 1995.

BACKGROUND OF THE INVENTION

1. Field of the Invention

This invention relates to containers, particularly pouches and bags, for containing objects to be sterilized and for holding sterilized objects free from contamination.

2. Brief Description of the Prior Art

Sterilization containers, such as pouches or bags, have been employed for containing objects to be sterilized by chemical sterilants and/or steam. The materials from such containers are made must include at least some portion that is permeable to the sterilizing medium but yet impermeable to ambient contaminants after the containers are removed from the sterilizing environment. A number of satisfactory materials have been proposed from which such sterilizing containers may be constructed.

Typically, however, the structure of such sterilizing containers has been such that the containers, once used, must be cast aside for disposal and replaced by additional containers. Satisfactory sterilizing containers which may be reused several times, which can be closed and reopened several times, have heretofore not been produced. It is a requirement of sterilizing containers that their integrity must be so high that one can be assured that an object, such as a dental or surgical instrument, will remain sterile even when an object-holding container, that has been sterilized, is stored away in a non-sterile ambient environment. Heretofore, it has been thought that the only acceptable way to insure the integrity of such containers was to construct the containers with a closure system could only be closed once so that, on being opened, the closure system was not reusable. Hence, sterilizing containers that employed such useonce closure systems had to be discarded upon being opened.

SUMMARY OF THE INVENTION

It is a primary object of the present invention to provide a sterilizing container that can be reused several times. Accordingly, it is a further object to provide such a container with a closure system that can be closed and opened several times without deleteriously affecting the integrity of the container. Another object is to provide such a container with means by which the number of times that the container has been reused can be recorded.

In accordance with these objects, the invention provides a sterilization container comprising first and second sheet means that are sealed together along side and bottom edges so as to provide an opening along an unsealed top edge into a storage space for an object to be sterilized between the two sheet means. The closure means is located outwardly of the opening and is extended transversely across the top edge, the closure means comprising an elongated metal strip extended through an enclosed channel. The strip extends beyond the channel so as to provide exposed strip ends. The closure means is located adjacent to the opening so that the closure means may be folded down across the opening and the strip ends bent around the closure means folds and against one of the sheet means whereby the opening may be sealed from the ambient. The closure means is located above and adjacent to the opening so that the closure means may be folded down across the opening so as to create several spirallyconcentric folds in upper portions of the first and second sheet means with the closure means positioned within the folds. The strip ends are bendable so that they may be bent around the folds and against one of the sheet means so that the folds are pressed against one of said sheet means, whereby the opening may be sealed from the ambient.

BRIEF DESCRIPTION OF THE DRAWINGS

FIG. 3 is a partial, detail plan view of the closure system of the FIG. 1 container;

FIG. 4 is a partial, detail cross-section view, taken along the line 4—4 of FIG. 3, illustrating the structure of the opening into the FIG. 1 container and the closure system relative to the opening;

FIGS. 5—8 illustrate, progressively, the manipulation of the invention's closure system from the open condition illustrated in FIG. 4 to the completely closed condition illustrated in FIG. 8;

FIGS. 5a, 6a, 7a, 8a illustrate, progressively, the manipulation of the invention's closure system from the open condition illustrated in FIG. 4 with a slightly different folding mode than the folding mode illustrated in FIGS. 5–8a;

FIG. 9 is a perspective view illustrating the course of the plastic film is the heat-sealing/bonding operation in the manufacture of the pouch of FIG. 1;

FIG. 10 is a side elevation view of a schematic depiction of the system for accomplishing the operation of FIG. 9;

FIG. 11 is a partial view of the open end of the pouch after production by the FIGS. 9 and 10 operation and system;

FIG. 12 is a side view of a schematic depiction of the system for providing a closure strip for the closure system of the FIG. 1 pouch;

FIG. 13 is a partial view of the open end of the pouch after production by the FIG. 12 system; and FIG. 14 illustrates the insertion of the closure strip to complete fabrication and assembly of the FIG. 1 pouch.

DESCRIPTION OF THE PREFERRED EMBODIMENT

Figure 1:
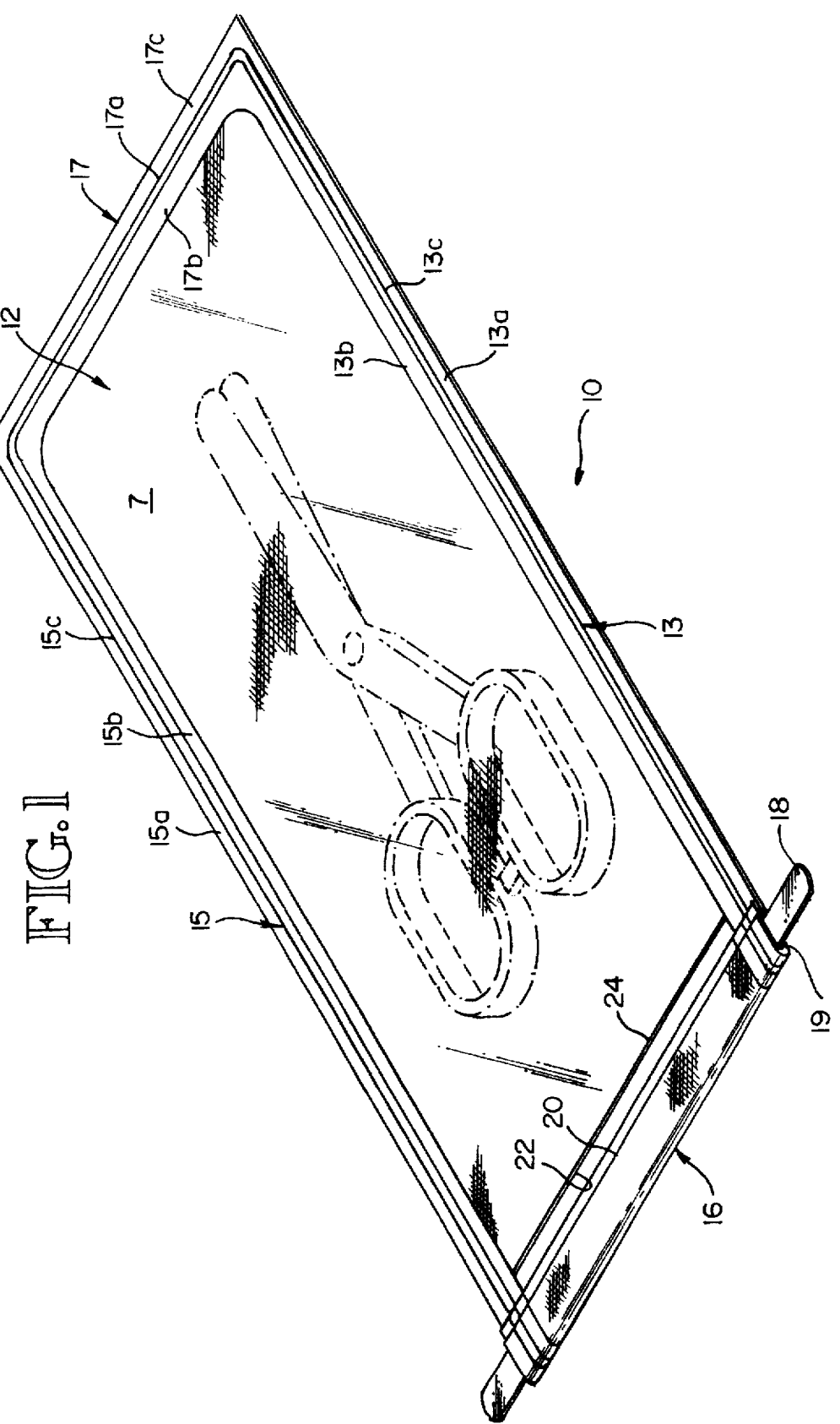
FIG. 1 illustrates a preferred form of the sterilizing container of this invention, in the form of a pouch or bag, in perspective with an object, a pair of scissors, contained therein.

The preferred form of the sterilizable container of this invention is that of a pouch or bag. The closure system of this invention, however, is not limited to application to a pouch or bag. Considering FIGS. 1–4, the preferred pouch 10 of this invention comprises a pair of sheets 7, 9 that provide first and second sides 12, 14 of the pouch and a closure means 16. The sheets are edge-bonded along both side edges and along the bottom edge to provide sealing seams 13, 15 and 17, respectively. The closure means 16 comprises a transverse open-ended channel 19 extended across the top of the pouch and a closure strip 18 that is inserted through the channel 19. Channel 19 is large enough that closure strip 18 can be manually inserted therethrough; channel 19 may be slightly larger, but it should not be so large that closure strip 18 would be so loosely contained that it could fall out of the channel when the pouch 10 is held or tilted on edge. Channel 19 is formed by doubling or folding one end of the sheet 9, comprising side 14, back onto itself and edge-bonding the overlap to provide a transverse seam 20. Closure strip 18 is preferably provided as a narrow, thin, rectangular strip of stainless steel with rounded corners. The pouch is closed by folding the closure means 16 down several times and crimping the strip 18 around the ends of the folds and against the back side 14.

An opening into pouch 10 is provided by an unsealed transverse edge 24 of the other sheet material 7, comprising side 12. Edge 24 is juxtaposed to a parallel edge 22 of the overlapped (folder over) portion side sheet material 9 of side 14 adjacent to the closure seam 20. Opening edge 24 extends between the side seams 13, 15. Adjacent edges 22, 24 are in close proximity to one another, as are edges 22 and transverse closure seam 20. "Close proximity" is defined as edges 22, 24 and seam 20 being close enough to one another that the opening edge 24 will be covered when channel 19 is folded once down over edge 24.

Figure 2:
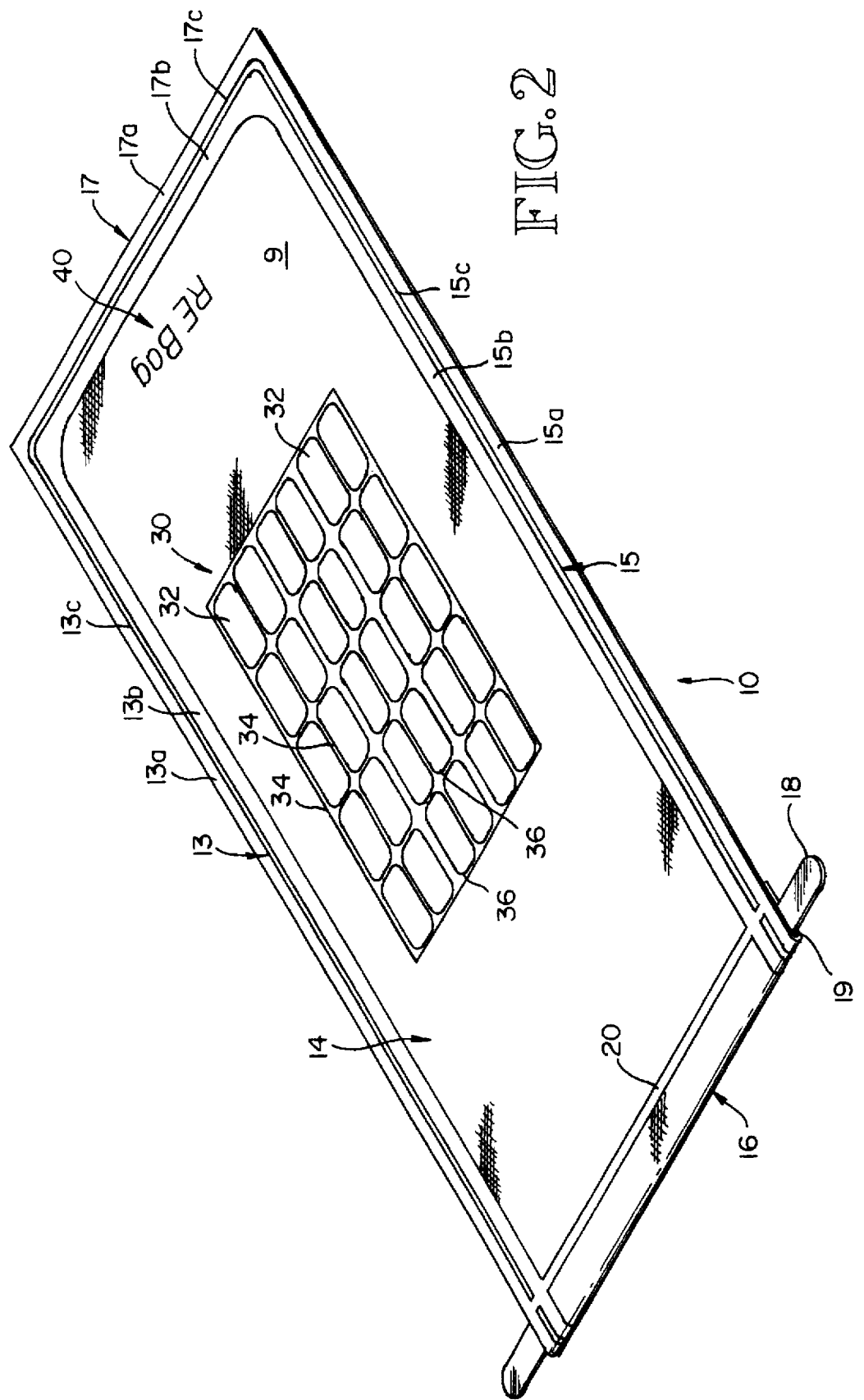
FIG. 2 is another perspective view of the FIG. 1 container, illustrating the opposite side of the container.

The side and bottom edge sealing seams 13, 15 and 17 are preferably provided as two spaced-apart sealed areas, 13a–13b, 15a–15b, and 17a–17b, that are separated by an unsealed rib 13c, 15c and 17c. At the bottom corners of the container 10, the sealed areas and unsealed ribs join so that the sealed areas are continuous and uninterrupted. This form of "rib seal" is shown in FIGS. 1 and 2.

To close the pouch opening, as defined by opening edge 24, the closure means 16 is folded down over the opening edge 24 in a sequence of steps as illustrated in FIGS. 5–8 and in FIG. 5a–8a. The differences between the folding modes illustrated in FIGS. 5a–8a relative to FIGS. 5–8 are explained in a later section. When the closure means 16 is folded, edge over edge, several times, preferably at least three or four times, (three folds being illustrated in FIGS. 5–7 and FIGS. 5a–7a) the protruding ends of strip 18 are bent back around the folds and against the opposite side 14 as shown in FIGS. 8 and 8a. Strip 18, as thus bent back around the folds and against the material of sheet 9, binds the layers of the folds tightly together to seal the pouch opening from the ambient.

The materials from which container 10 are fabricated are capable of being re-used a number of times. That is to say, the structural integrity of the pouch 10 is maintained over the course of a number of sterilizing cycles where the pouch is opened, the sterile contents removed, unsterile objects inserted within the pouch, the pouch resealed and re-sterilized. In the preferred embodiment of the container 10, the cycle can be repeated in excess of thirty times. Over the course of reuse, however, the strip 18—albeit made of stainless steel—may become awkward to use because of its protruding ends being bent out of shape as it is bent to clasp the pouch as shown in FIG. 8 and 8a and as it is straightened to open the pouch. By reason of the provision of strip 18 as an unattached element, the strip can be replaced with a new strip simply be withdrawing the old strip from the elongated channel 19 and inserting the new strip through channel 19. Some users may even prefer to replace a used strip after each use so that each pouch closing operation employs an unused strip.

One side of pouch 10 is preferably provided with an embossed area which can be used to record actual times that the pouch was reused. FIG. 2 illustrates an embossing 30 on side 14 for this purpose. Embossing 30 comprises an array of rectangular boxes 32, arranged in five rows of six columns each, in which the date of use of the pouch for sterilizing objects can be recorded. As thus illustrated, thirty dates can be recorded to reflect thirty sterilizing episodes to which the pouch was exposed. The array of boxes 32 can be defined by several longitudinal embossed ribs 34 intersected by several transverse embossed ribs 36, the boxes being composed of the non-embossed areas between the intersecting ribs 34, 36. Suitable markings of the user's choice can be made within each of the boxes 32 with a marking instrument. The embossing 30 may be located at any convenient location on side 14, and a portion of side 14 toward the bottom of the pouch can be reserved for the embossing of a trade mark 40 or other suitable identification as chosen by the pouch's manufacturer such as a model number or the like.

In the preferred form of pouch 10, the sheets 7, 9 are provided of thermoplastic material that may be heat and pressure bonded to one another to provide seams 13, 15 and 17. As a consequence, sheet 9 would also be heat and pressure bondable to itself so as to provide seam 20. Furthermore, the preferred materials are selected to provide sheet 7 of a transparent, impervious material, and to provide sheet 9 of an opaque, pervious material; with sheet 14 being selectively pervious to a sterilizing medium such as a sterilizing gas or steam but not pervious to ambient contaminants such as bacteria. A number of thermoplastic polymers have been proposed as suitable for use as a transparent thermoplastic sheet material in sterilizing containers, and therefore potentially suitable for sheet 7; such as polyolefinic transparent films such as polyethylene, polypropylene, or blends thereof, polyethylene terephthalate such as that known as MYLAR, nylon, or a laminate of polyethylene terephthalate and polypropylene. Such thermoplastic material would be provided as a film having suitable thickness and thermal characteristics as to be sufficiently impervious to the ambient to block passage of bacteria and other contaminants. A number of thermoplastic polymers have been proposed as suitable for use as an opaque thermoplastic sheet material in sterilizing containers, and therefore potentially suitable for sheet 9; such as synthetic or artificial paper-like materials such as those comprising spun-bonded polyethylene known as TYVEK, or a non-woven fabric comprised of thermoplastic fibers or filaments which may be composed of polypropylene. Such thermoplastic material would have suitable thickness and thermal characteristics as to be sufficiently impervious to the ambient to block passage of bacteria and other contaminants, and yet be pervious to sterilants media such as ethylene oxide or steam.

The preferred construction of pouch 10 is provided by clear polypropylene film for side 12 and an opaque, non-woven fabric of polypropylene for side 14. The fabric-like character of non-woven polypropylene provides the necessary limited, or selective, perviousness that is required; and being of the same base material as the clear polypropylene sheet for side 12, the two sides have very similar thermal characteristics such as melting points and the like so that the two sides 12, 14 can be conveniently and easily heat and pressure bonded together to provide the side and bottom edge seams 13, 15 and 17. A suitable non-woven polypropylene fabric can be produced by the method described in U.S. Pat. No. 4,041,203, comprising a laminate of melt-blown thermoplastic polypropylene microfibers and a layer of spunbonded thermoplastic polypropylene filaments united by a patterned application of heat and pressure that produces a waffle-like affect. This non-woven fabric is impervious to bacteria and many other contaminates, but is pervious to sterilants such as ethylene oxide and to steam. In summary, sheet 7 will be smooth and of a nature to be impervious to both sterilizing media and to contaminants such as bacteria; and sheet 9 will be rougher, fabric-like, and hence pervious to sterilizing media but impervious to contaminants such as bacteria.

In the preferred embodiment of the pouch wherein sheet 9 is fabricated of a non-woven polypropylene fabric, the outer edge heat-sealed seam, composed of side and bottom seams 13a, 15a and 17a, is a narrow heat-sealed strip or rib that bonds the edges of sheets 7 and 9 clear out to the outer edges of the pouch. This outer edge heat-sealed seam completely traverses the two side edges and the bottom edge of the pouch. Furthermore, the inner edge heat sealed seam, composed of side and bottom seams 13b, 15b and 17b, is a narrow heat-sealed strip or rib that extends parallel to the outer edge heat-sealed seam but that is spaced a distance inbound from the edges of sheets 7 and 9 so that there is a substantial width of unbonded material between the inner and outer edge heat-sealed seams; this width being at least as great as the width of each one of the two sealed edge seams and preferably about twice as wide. This inner edge heat-sealed strip terminates, as shown in FIG. 3 at 13b' and 15b', short of the opening into the pouch as defined by unsealed transverse edge 24 of sheet 7. Consequently, the rib seal affect provided by the inner and outer seams is effective when the closure means 16 closes off the opening into the pouch as heretofore described since the folded and clamped opening (as seen in FIGS. 8 and 8A) effectively overlap the terminus 13b' and 15b' of the inner edge seal. As a result of this rib seal configuration, wherein the outer edge seal extends completely across the closure means portion of the pouch (FIG. 3) but the inner edge seal terminates short of the pouch opening (FIG. 3), the necessary flexibility of the pouch material in the vicinity of the pouch opening is maintained so that the pouch can be opened and closed numerous times without damage to the rib seal. If the inner edge seal extended across the channel 19, and/or if the gap between the inner and outer edge seals were too narrow, the heat-sealed portions of the non-woven fabric of sheet 9 might be too brittle to withstand numerous openings and closings.

The rib seal affect provided by the use of the inner and outer edge seals as aforedescribed provides an additional function. When manufactured in bulk quantities, numerous individual pouches would be produced, both simultaneously and sequentially, in a large sheet with adjacent edges sharing a common outer edge seal rib. Then individual pouches would be sheared from the common sheet by an anvil-type cutter mechanism. It has been found to be highly advantageous to sever the non-woven fabric, of which side 9 is composed, by an anvil-type cutter mechanism by severing the material longitudinally through a heat-sealed rib area. To do otherwise poses the likelihood that the non-woven fabric would not be sheared properly. Furthermore, the narrow inner edge seal rib is completely adequate to maintain a sterile environment within the closed and sterilized pouch. The outer edge seal rib is not required to maintain the desired degree of pouch security; its primary purpose is to ensure that numerous pouches can be satisfactorily severed from one another during the manufacturing process.

Referring to FIGS. 9 and 10, rolls of plastic film stock 1 and 2 are provided to produce the two sides 7 and 9 of the pouch. In the operation shown in FIG. 9, the width of the film stock is sufficient to produce two end-to-end pouches simultaneously that may thereafter be severed and completed in a separate operation to the finished pouch of FIGS. 1 and 2. The length of the film stock is sufficient to produce numerous duplicates of the end-to-end pouches ("pouch pairs" 3, each duplicate pair 3 being arranged side-to-side with adjacent pairs. The sheet 2 is provided in a greater width that sheet 1 and the two sheets are overlapped so that sheet 1 is centered between the edges of sheet 2 as depicted in FIG. 9 in dotted line. The outwardly-extending edge portions of sheet 2 will be employed to form the clasp channel 9 in a manner described later.

Each pair 3 is produced by a metal thermal-welding die that is formed to simultaneously provide the outer side and outer end seals 13a, 15a and 17a and the inner side and end seals 13b, 15b and 17b of both pouches of the pair 3 simultaneously in the operation and system of FIGS. 9 and 10. In FIG. 9, three pairs are illustrate still connected to the film stock 1 and 2; one pair 3 is illustrated separated from the film stock, but still joined end-to-end; and one pair are illustrated after being severed from one another to produce two incomplete pouches 4. The die is formed so that a common thermal-welded seam is provided at the end-to-end juncture of the pair as indicated at 5a with respect to the pair 3. The die is part of a welding operation 50 (FIG. 10) where the die reciprocated vertically downward from a resting position (shown in FIG. 10) to a welding position where the film stock is clamped between the die and a forge plate 52 for welding the film stock together to produce the aforementioned seams. The film stock is advanced in a timed sequence with respect to the reciprocation of the die by a film advancing operation 54. The film is advanced by operation 54 a distance sufficient to shift a just-formed pouch pair forward of the welding operation 50 thereby bringing a fresh section of the film stock into position for welding. Preferably, the forward shift of the film stock by operation 54 is just sufficient to cause the adjacent outer side seams of two adjacent pouch pairs (indicated at 5b and 5c in the separated pouch pair 3) to be immediately adjacent to—or even touching—one another so that upon severing into discrete pouch pairs 3, the severed edges (indicated at 5b and 5c) will have occurred in the welded outer side seam. To insure that this occurs, it may be desirable that the forward shift of the film stock by operation 54 by just slightly less than the width of the pouch pair so that there is a very slight overlapping of the die onto a just-formed outer side seam weld; the result being a common thermal-welded seam as indicated at 5d and 5e between immediately adjacent pouch pairs. As shown in FIG. 10, the sheets of film stock 1 and 2 are brought into overlapping relation to one another and thermal-welded together multiple times at operation 50 as a consequence of the timed advancement of the overlapped film stock by operation 54. At the conclusion of the operation as illustrated in FIG. 10, the pouch pairs are severed from one another by severing operation 56 to produce individual pouch pairs 3. The severing operation 56 operates to cut the pouch pairs apart along the common welded seam (eg as at 5d or 5e) while the overlapped film stock is stationary between advancement/welding cycles.

When the welding operation 50 is actuated to bring the die into contact with the film stock, the application of heat and pressure to the overlapped film stock must be applied for a sufficient duration to effect the welding of the two film stock materials together. Operation 50 involves heating the die to a suitable welding temperature; this die heating may be intermittent and timed so that the die is hottest during welding. During this period, the film stock would be stationary in the system and it is at this time that the severing operation 56 is actuated to sever a pouch pair from the continuous web 60 of pouch pairs upstream from the severing operation. When the duration required for bonding is completed, the die is vertically translated up away from the forge 52, releasing the web 60. Then advancing operation 54 is actuated to advance the web forward toward the severing operation 56; whereupon the cycle repeats. Advancing operation 54 may be provided by upper and lower clamps 58 that are vertically translated toward one another from opposite sides of web 60 to engage and clamp the film stock sheets together, and then the engaged clamps 58 are shifted forward to advance the web. Following advancement, the clamp 58 would be vertically translated to disengage from the web and then the disengaged clamps would be shifted rearwardly to their point of beginning; whereupon the cycle repeats. The vertical and horizontal translation of the clamps 58 is indicated by vertical and horizontal arrows in FIG. 10, and by the solid and dotted line positions of clamps 58.

Just prior to the point at which the two sheets from film stock 1 and 2 are brought together at 70, an embossing operation 62 is actuated to imprint the calendar grid embossing 30 onto the film stock 2 in the appropriate locations for the to-be-formed pouch pairs. This operation 62 is timed so that the embossing occurs during the time that the welding operation is actuated at 50. Because only the pouch sheet 9 is to be embossed, this embossing operation is most conveniently located upstream of the overlapping of the sheets of the film stock 1 and 2. An embossing die is translated vertically to engage and disengage the top sheet from film stock 2 and to press it against an embossing forge 64. Operation 62 involves heating the die to a suitable welding temperature; this die heating may be intermittent and timed so that the die is hottest during embossing. The embossing temperature and pressure would be lower than the welding temperature and pressure at operation 50.

In order to protect the integrity of the plastic film sheets, both sheets are sandwiched between upper and lower courses of TEFLON film 70, 72. Each course 70, 72 may be provided as an endless loop as shown in FIG. 10 is brought into engagement with the plastic film sheets from film stock 1 and 2, and taken out of engagement therewith, as indicated at 73, 74, 75, 76. TEFLON is not subject to melting or degrading at the temperatures at which the embossing and welding operations 62, 50 take place. Because the welding temperature is high enough to liquify the film from film stock 1 at the weld seams, the TEFLON film is conveniently located above and below the web 60 from just prior to the welding operation 50 until just prior to the severing operation 56.

Following the operation and system of FIGS. 10 and 11, the pouches of each pouch pair 3 are severed from one another and then passed through a clasp channel-forming operation 80 illustrated in FIG. 12. Here, the outer end of the sheet 9 (see FIG. 11) is doubled back on to itself as shown in FIG. 12 with its outer edge 22 and close adjacency with the open outer edge 24 of sheet 7. Then a heated die is brought against the overlapped portions of the sheet 9 to weld the two together to provide the seam 20 and closure strip channel 19.

Referring now to FIGS. 1–8, it is important to the structure of the pouch's closure means 16 that the pervious side 14 not have a smooth surface similar to side 12. As can be seen from the step-wise sequence of FIGS. 4–7, the first fold shown in FIG. 5 brings the two dissimilar materials of sides 12 and 14 in contact with one another at the commencement of the opening into the pouch as defined be opening edge 24. Continued folding as shown in FIGS. 6 and 7 bring the adjacent materials of sides into greater contiguous contact. This folding of the two dissimilar materials together not only further isolates the opening of the pouch from the ambient, but it also insures that ambient contaminants cannot travel between the adjacent dissimilar materials along the convoluted path to the opening into the pouch, the material of fabric-like character of side 14 being pressed against the smooth surface of the material of side 12, beginning at the opening edge 24. If the two sides 12, 14 were composed of similar smooth-surfaced materials, the contact between them as the closure means was folded down as shown in FIGS. 5–7 would not so-assuredly produce the required degree of sealing as is accomplished because of the dissimilar character of the two surfaces; one being smooth and the other rougher and more fabric-like.

Transverse seam 20 extends across both side seams 13, 15 and has a width that is narrower than the spaced-apart sealed areas of the side seams. Transverse seam 20 is stiffer than the surrounding portions of the sheet 9 that define the channel 18. Consequently, seam 20 provides a natural bending line about which the closure means 16 may be first folded down onto the face of sheet 9. As shown in FIG. 5, that first fold is made about the lower edge of seam 20, the lower edge of seam 20 providing the bending line. However, the upper edge of seam 20 could provide the bending line, in which case the position of strip 18 relative to the upper edge 24 of sheet 7 would be shifted upward from the position shown in FIG. 5. The edges 22, 24 and seam 20 must be in close enough proximity that the folded-over portion of sheet 9 will overlay opening edge 24 when the upper edge of seam 20 provides the bending line. This latter configuration is illustrated in FIG. 5a. Making the first fold of the closure means 16 with the bottom edge of seam 20 providing the bending line provides an adequate start of the pouch sealing progression illustrated in FIGS. 5–7. However, juxtaposing the pouch-opening edge 24 with the mid-portions of the channel 19 and strip 18 will provide an even more effective seal. Because the opening edge 20 will be positively contacted by the material from which sheet 9 is made, the opening to the pouch 10 is more effectively sealed closed, commencing at the opening edge 20. This is illustrated in FIGS. 6a and 7a. Nevertheless, the closure illustrated in FIGS. 5–7 is effective since the opening to the pouch 20 is effectively sealed closed downward from the opening edge 20. Whichever mode of closure is effective, whether using the upper or lower edge of seam 20 as the bending edge, the relative location of seam 20 effectively serves as an automatic guide and aid to the user to ensure that the pouch opening is effectively closed by the closure means 16.

While the preferred embodiment of the invention has been described herein, variations in the design may be made. The scope of the invention, therefore, is only to be limited by the claims appended hereto.

The embodiments of the invention in which an exclusive property is claimed are defined as follows:

1. A sterilization container comprising first and second sheet means that are sealed together along side and bottom edges so as to provide a storage space for an object to be sterilized and so as to provide an unsealed top edge of said first sheet means that defines an opening into said storage space, said second sheet means having an upper portion that is extended beyond said top edge; and closure means located outwardly of said opening and extended transversely of said top edge for closing said opening, said closure means comprising an elongated strip positioned across said portion transverse to said opening, said strip extending beyond the side edges of said second sheet so as to provide exposed strip ends; said closure means being located above and adjacent to said opening so that said closure means may be folded down across said opening so as to create several spirally-concentric folds in upper portions of said first and second sheet means with said closure means positioned within the folds; said strip ends being bendable so that they may be bent around said folds and against one of said sheet means so that said folds are pressed against said one of said sheet means, whereby said opening may be sealed from the ambient; said first sheet means being fabricated from a clear thermoplastic film capable of being heat and pressure bonded to form side and bottom edge seals and said second sheet means being fabricated from an opaque non-woven fabric of thermoplastic fibers or filaments capable of being heat and pressure bonded to form side and bottom edge seals; said first and second sheet means being heat-sealed along their entire respective side and bottom edges by a first heat-sealed strip and being heat-sealed along a second inner heat-sealed strip that extends parallel to said first heat-sealed strip and terminates within said first sheet means short of and adjacent to the top edge of said first sheet means.

2. The container of claim 1 wherein the upper portion of said second sheet means is folded down and sealed to itself along a transverse seam to provide a channel within the folded-over portion of said second sheet means for receiving said closure means, said transverse seam being positioned above said top edge and providing a bending line so that said closure means may be folded along said bending line to overlay said top edge whereby said opening may be sealed from the ambient.

3. The container of claim 2 said second sheet means includes an upper edge that is located above and adjacent to said first sheet means upper edge and between said transverse seam and said first sheet means upper edge so that said opening is unobstructed by said closure means when said closure means is in an unfolded condition.

4. The container of claim 1 wherein one of said sheet means is provided with an embossing providing areas suitable for marking so as to record indicia indicating the number of times said container has been sterilized.

5. The container of claim 2 wherein one of said sheet means is provided with an embossing providing areas suitable for marking so as to record indicia indicating the number of times said container has been sterilized.

6. The container of claim 1 wherein said first sheet means comprises a polypropylene film; and wherein said second sheet means comprises a laminate of a web of spunbonded polypropylene filaments and a web of polypropylene microfibers.

* * * * *